US010258508B2

(12) United States Patent
Bar-On

(10) Patent No.: US 10,258,508 B2
(45) Date of Patent: Apr. 16, 2019

(54) APPARATUS AND METHOD FOR REMOVING CORNEAL EPITHELIUM

(71) Applicant: ORCA SURGICAL LTD., Caesarea (IL)

(72) Inventor: Yariv Bar-On, Yavne (IL)

(73) Assignee: ORCA SURGICAL LTD., Caesarea (IL)

(*) Notice: Subject to any disclaimer, the term of this patent is extended or adjusted under 35 U.S.C. 154(b) by 60 days.

(21) Appl. No.: 15/508,131

(22) PCT Filed: Sep. 4, 2015

(86) PCT No.: PCT/IL2015/050894
§ 371 (c)(1),
(2) Date: Mar. 2, 2017

(87) PCT Pub. No.: WO2016/035087
PCT Pub. Date: Mar. 10, 2016

(65) Prior Publication Data
US 2017/0281413 A1  Oct. 5, 2017

Related U.S. Application Data

(60) Provisional application No. 62/045,655, filed on Sep. 4, 2014.

(51) Int. Cl.
A61F 9/013       (2006.01)
A61F 9/007       (2006.01)

(52) U.S. Cl.
CPC ............. A61F 9/013 (2013.01); A61F 9/007 (2013.01); A61F 9/0133 (2013.01)

(58) Field of Classification Search
CPC .......... A61B 17/3209; A61B 17/32093; A61B 17/3211; A61B 17/3213; A61F 9/007;
(Continued)

(56) References Cited

U.S. PATENT DOCUMENTS 5,722,945 A    3/1998  Anis et al.
6,149,661 A    11/2000 Graczyk
(Continued)

FOREIGN PATENT DOCUMENTS

JP    2003175071 A    6/2003
WO       9422402 A1   10/1994

OTHER PUBLICATIONS

International Search Report PCT/IL2015/050894 Completed Jan. 7, 2016; dated Jan. 10, 2016 5 pages.
(Continued)

Primary Examiner — Todd J Scherbel
Assistant Examiner — Andrew P. Restaino
(74) Attorney, Agent, or Firm — The Roy Gross Law Firm, LLC; Roy Gross

(57) ABSTRACT

A device comprising: an elongated head having a distal end formed by an elongated edge of a cutting blade positioned in parallel with an elongated edge of a control blade, wherein the elongated edges of the respective control and cutting blades are separated by a uniform gap forming the distal opening to a channel running from an anterior end to a posterior end of the head, wherein the elongated edge of the cutting blade extends distally beyond the elongated edge of the control blade providing a height differential between the edge of the cutting blade and the edge of the control blade, wherein the edge of the cutting blade is sharp and configured to cut a bodily tissue, and wherein the edge of the control blade is dull and forms a barrier that limits the depth of penetration of the edge of the cutting blade into the bodily tissue.

18 Claims, 6 Drawing Sheets

(58) Field of Classification Search
CPC .............. A61F 9/00736; A61F 9/00754; A61F 9/00781; A61F 9/013; A61F 9/0133; A61F 9/0136; A61F 2009/00868
USPC ......................................................... 606/166
See application file for complete search history.

(56) References Cited

U.S. PATENT DOCUMENTS

| | | | |
|---|---|---|---|
| 7,374,566 B1 * | 5/2008 | Schossau .............. | A61F 9/0133 606/107 |
| 7,901,404 B2 * | 3/2011 | Reay-Young ...... | A61B 17/1604 606/79 |
| 2006/0047255 A1 | 3/2006 | Kiehlbauch et al. | |
| 2008/0195127 A1 * | 8/2008 | Bar-On ................ | A61F 9/0133 606/166 |
| 2010/0185224 A1 * | 7/2010 | Wu ........................ | A61B 17/00 606/182 |
| 2013/0211395 A1 * | 8/2013 | Schwartz ............ | A61F 9/00745 606/28 |

OTHER PUBLICATIONS

Written Opinion of the International Searching Authority PCT/IL2015/050894 dated Jan. 10, 2016 5 pages.

* cited by examiner

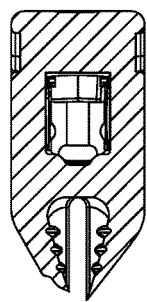
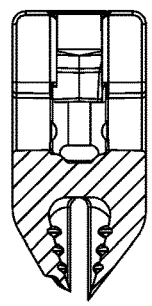
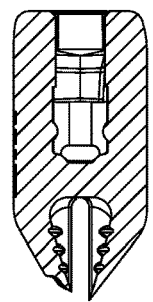
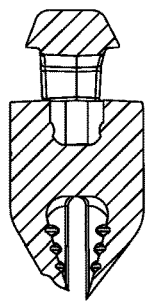
SECTION M-M  SECTION L-L  SECTION K-K  SECTION J-J
FIG.2A  FIG.2B  FIG.2C  FIG.2D
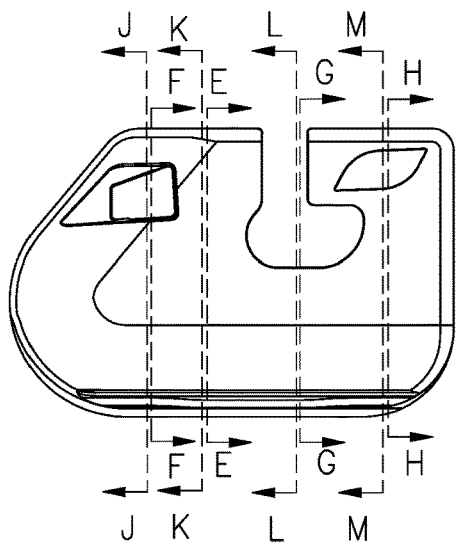
FIG.2E
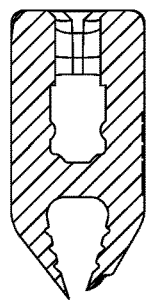
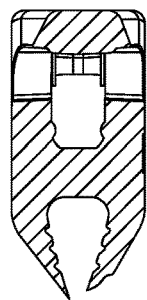
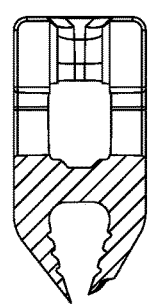
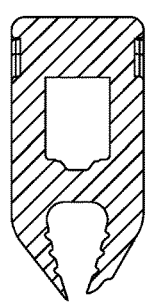
SECTION E-E  SECTION F-F  SECTION G-G  SECTION H-H
FIG.2F  FIG.2G  FIG.2H  FIG.2I

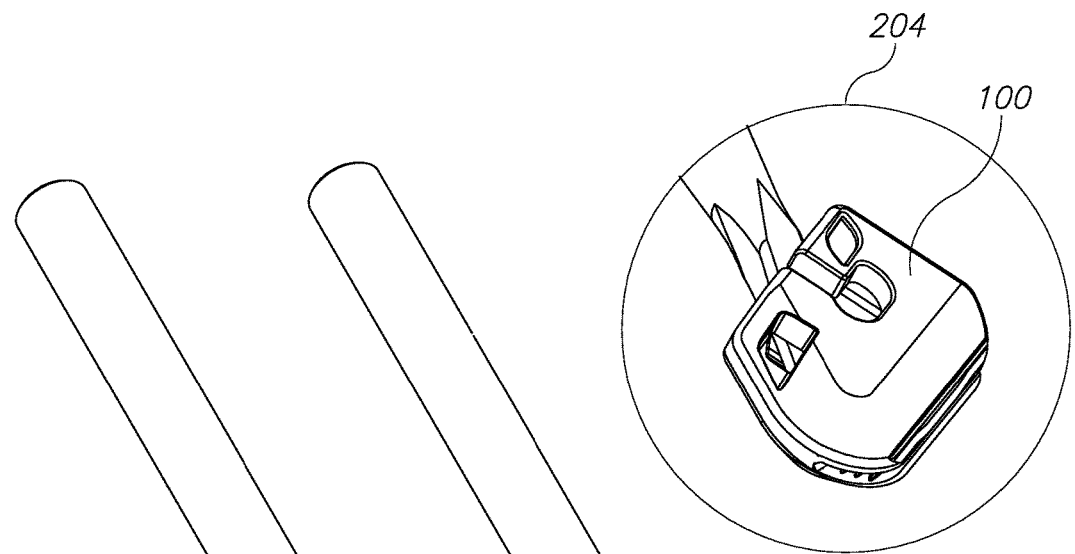
FIG.3C
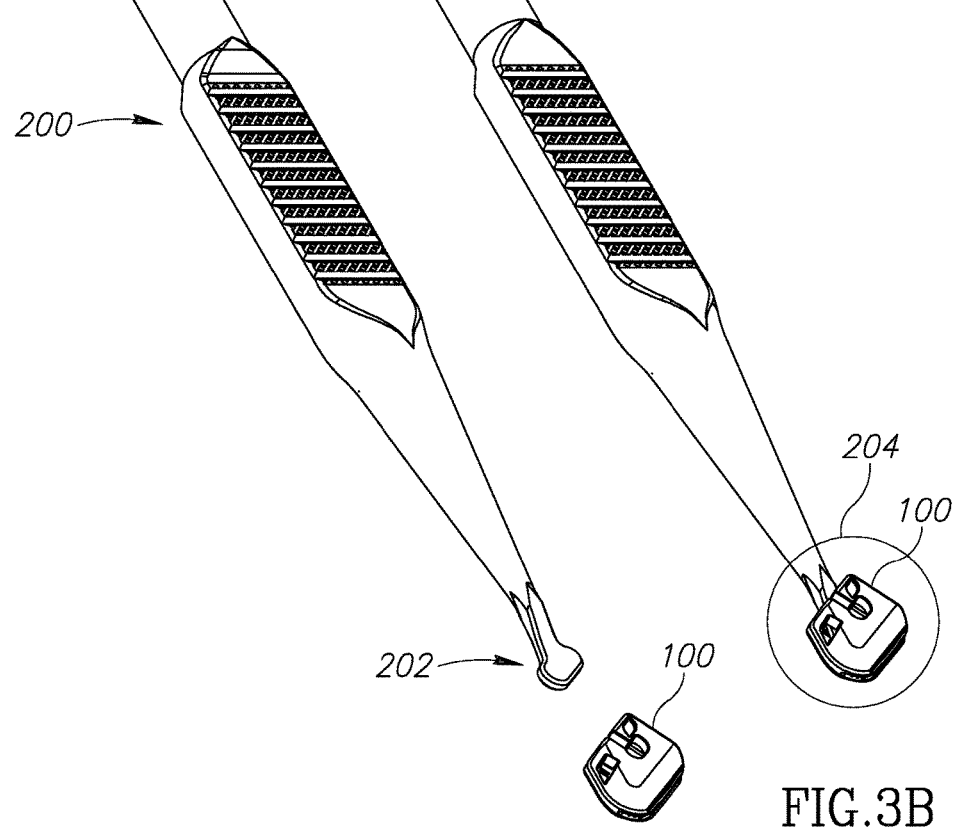
FIG.3B
FIG.3A

APPARATUS AND METHOD FOR REMOVING CORNEAL EPITHELIUM

CROSS-REFERENCE TO RELATED APPLICATIONS

This application is a national phase of PCT Patent Application No. PCT/IL2015/050894, filed Sep. 4, 2015, which claims the benefit of U.S. Provisional Patent Application No. 62/045,655 filed Sep. 4, 2014 and entitled "Apparatus and Method for Removing Corneal Epithelium", the contents of both application being which are incorporated herein by reference in their entirety.

BACKGROUND

The invention relates to the field of ophthalmology.

The cornea is a transparent epithelium layer covering the iris, pupil and anterior chamber of the eye. Incoming light is refracted by the curvature of the cornea, contributing to the eye's focusing power. The cornea is typically circular in shape, with a diameter of approximately 10 mm and thickness ranging from 50-70 µm, that rests on top of the Bowman's membrane or layer, which in turn covers the major corneal stroma. The epithelium is a layer of fast growing and easily regenerated cells that blocks the passage of foreign bodies and provides a smooth surface for distributing oxygen and nutrients from tears. Although the epithelium has no blood cells it does have nerve cell endings. An eroded, cut, damaged, dystrophied or diseased corneal epithelium can be removed to regenerate itself in about 2-3 days. However, while the epithelium is regenerative, the underlying Bowman's membrane is not.

The epithelium may also be removed as a precursor to laser refractive surgery, which is a corrective eye surgery that utilizes an excimer laser to change the curvature of the cornea in an effort to correct myopia, hyperopia and astigmatism. Lately, more complex ablation patterns have allowed for the correction of higher order aberrations. A fundamental step during the surgery is symmetric, rapid removal of the central and paracentral corneal epithelium, or skin layer of the cornea, to enable the laser to reshape the corneal stroma, where consistency in performing this procedure directly impacts on the results. Ideally, the epithelium is sufficiently removed to support the larger diameter of modern day excimer lasers while not exceeding an amount that would prolong healing time and increase the risk of infection.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a device comprising: an elongated head having a length ranging between 5-13 millimeters, and having a distal end that has a length ranging from 4-10 millimeters formed by an elongated edge of a cutting blade positioned substantially in parallel with an elongated edge of a control blade, wherein the elongated edges of the respective control and cutting blades are separated by a substantially uniform gap having a width ranging between 0.02 to 0.2 mm and forming the distal opening to an elongated channel running from an anterior end to a posterior end of the head, and wherein the elongated edge of the cutting blade extends distally beyond the elongated edge of the control blade providing a height differential ranging from 0.05-0.5 mm between the elongated edge of the cutting blade and the elongated edge of the control blade, and wherein the elongated edge of the cutting blade is sharp, having outer edges forming an acute angle ranging between 10°-50°, and configured to cut a bodily tissue, and wherein the elongated edge of the control blade is dull, having outer edges forming a rounded corner with a radius ranging from 0.05 mm-0.1 mm, and configured to form a barrier that limits the depth of penetration of the elongated edge of the cutting blade into the bodily tissue.

In some embodiments, the elongated edge of the control blade comprises a band having a non-uniform height differential with respect to the elongated edge of the cutting blade.

In some embodiments, a combination of the width of the gap and the height differential defines the depth of penetration of the edge of the cutting blade.

In some embodiments, the orientation of the angle of the head with respect to a surface of the bodily tissue further defines the depth of penetration of the edge of the cutting blade.

In some embodiments, the height differential is smaller at a middle section of the elongated edges of the control and cutting blades, and larger at a peripheral section of the elongated edges of the control and cutting blades.

In some embodiments, the elongated edge of the control blade is configured to press onto a cornea to flatten its surface, and wherein the gap is configured to enclose the flattened cornea and prevent the flattened cornea enclosed therein from bouncing back to a naturally convex shape.

In some embodiments, the elongated channel is enclosed by two oppositely facing inner walls of the control blade and the cutting blade.

In some embodiments, the inner walls are concave, and wherein the elongated channel formed by the concave inner walls has a sack-like cross section having a broad proximal base and a narrow distal opening, wherein the channel is configured to collect any combination of peeled epithelial tissue and released residue.

In some embodiments, the channel is at least partially coated with an absorbent substance that is suitable for absorbing fluid.

In some embodiments, the channel is disposed with one or more elongated grooves embedded in the inner walls of the channel and extending substantially parallel to the elongated edges of control and cutting blades and increasing the surface area of the inner walls of channel.

In some embodiments, the grooves are disposed at varying heights of the channel.

In some embodiments, the one or more grooves are disposed with an absorbent substance that is suitable for absorbing fluid.

In some embodiments, the device further comprises a handle, wherein the head is disposed with a proximal recess that is configured to engage with the handle.

In some embodiments, the proximal recess is configured to release the engaged handle.

In some embodiments, the handle is rigid and transfers a motion applied to the handle to the head.

In some embodiments, the head is disposed with one or more recesses that are configured to engage with one or more prongs that are configured to secure the head, and wherein the recesses are disposed at a proximal end of the head and engaging with the prongs comprises having no contact with the distal edges of the blades.

In some embodiments, the anterior end of the head is tapered and is formed by the externally convex anterior walls and rounded anterior distal corners of the control blade and the cutting blade.

In some embodiments, a portion of the anterior distal rounded corner of the control blade is hollowed out, forming a narrow groove comprising an anterior side opening of the channel.

In some embodiments, the bodily tissue is the cornea.

In some embodiments, the device further comprises a second control blade, wherein the cutting blade is a double-sided blade, and wherein the two control blades are disposed on either side of the double-sided cutting blade.

There is provided, in accordance with an embodiment, a kit comprising, one or more elongated heads having a length ranging between 5-13 millimeters wherein each elongated head has a distal end having a length ranging from 4-10 millimeters formed by an elongated edge of a cutting blade positioned substantially in parallel with an elongated edge of a control blade, and wherein the elongated edges of the respective control and cutting blades are separated by a substantially uniform gap having a width ranging between 0.02 to 0.2 mm and forming the distal opening to an elongated channel running from an anterior end to a posterior end of the head, and wherein the elongated edge of the cutting blade extends distally beyond the elongated edge of the control blade providing a height differential ranging from 0.05-0.5 mm between the elongated edge of the cutting blade and the elongated edge of the control blade, and wherein the elongated edge of the cutting blade is sharp, having outer edges forming an acute angle ranging between 10°-50°, and configured to cut a bodily tissue, and wherein the elongated edge of the control blade is dull, having outer edges forming a rounded corner with a radius ranging from 0.05 mm-0.1 mm, and configured to form a barrier that limits the depth of penetration of the elongated edge of the cutting blade into the bodily tissue; a handle; and a cassette comprising: a rotatable cartridge configured to store the one or more elongated heads and allow each elongated head to engage with the handle while leaving the edges of the control and cutting blades untouched.

In some embodiments, the elongated edge of the control blade comprises a band having a non-uniform height differential with respect to the elongated edge of the cutting blade.

In some embodiments, a combination of the width of the gap and the height differential defines the depth of penetration of the edge of the cutting blade.

In some embodiments, the orientation of the angle of the head with respect to a surface of the bodily tissue further defines the depth of penetration of the edge of the cutting blade.

In some embodiments, the height differential is smaller at a middle section of the elongated edges of the control and cutting blades, and larger at a peripheral section of the elongated edges of the control and cutting blades.

In some embodiments, the elongated edge of the control blade is configured to press onto a cornea to flatten its surface, and wherein the gap is configured to enclose the flattened cornea and prevent the flattened cornea enclosed therein from bouncing back to a naturally convex shape.

In some embodiments, the elongated channel is enclosed by two oppositely facing inner walls of the control blade and the cutting blade.

In some embodiments, the inner walls are concave, and wherein the elongated channel formed by the concave inner walls has a sack-like cross section having a broad proximal base and a narrow distal opening, wherein the channel is configured to collect any combination of peeled epithelial tissue and any released residue.

In some embodiments, the channel is at least partially coated with an absorbent substance that is suitable for absorbing fluid.

In some embodiments, the channel is disposed with one or more elongated grooves embedded in the inner walls of the channel and extending substantially parallel to the elongated edges of control and cutting blades and increasing the surface area of the inner walls of channel.

In some embodiments, the grooves are disposed at varying heights of the channel.

In some embodiments, the one or more grooves are disposed with an absorbent substance that is suitable for absorbing fluid.

In some embodiments, the kit further comprises a handle, wherein the head is disposed with a proximal recess that is configured to engage with the handle.

In some embodiments, the proximal recess is configured to release the engaged handle.

In some embodiments, the handle is rigid and transfers a motion applied to the handle to the head.

In some embodiments, the head is disposed with one or more recesses that are configured to engage with one or more prongs that secure the head, and wherein the recesses are disposed at a proximal end of the head and engaging with the prongs comprises having no contact with the distal edges of the blades.

In some embodiments, the anterior end of the head is tapered and is formed by the externally convex anterior walls and rounded anterior distal corners of the control blade and the cutting blade.

In some embodiments, a portion of the anterior distal rounded corner of the control blade is hollowed out, forming a narrow groove comprising an anterior side opening of the channel.

In some embodiments, the kit further comprises a second control blade, wherein the cutting blade is a double-sided blade, and wherein the two control blades are disposed on either side of the double-sided cutting blade.

In some embodiments, the bodily tissue is a cornea.

There is provided, in accordance with an embodiment, a method for modifying the corneal epithelium, comprising: peeling a portion of the corneal epithelium using an elongated head having a length ranging between 5-13 millimeters, and having a distal end having a length ranging from 4-10 millimeters formed by an elongated edge of a cutting blade positioned substantially in parallel with an elongated edge of a control blade, wherein the elongated edges of the respective control and cutting blades are separated by a substantially uniform gap having a width ranging between 0.02 to 0.2 mm and forming the distal opening to an elongated channel running from an anterior end to a posterior end of the head, and wherein the elongated edge of the cutting blade extends distally beyond the elongated edge of the control blade providing a height differential ranging from 0.05-0.5 mm between the elongated edge of the cutting blade and the elongated edge of the control blade, and wherein the elongated edge of the cutting blade is sharp, having outer edges forming an acute angle ranging between 10°-50°, and configured to cut the corneal epithelium, and wherein the elongated edge of the control blade is dull, having outer edges forming a rounded corner with a radius ranging from 0.05 mm-0.1 mm, and configured to form a barrier that limits the depth of penetration of the elongated edge of the cutting blade into the corneal epithelium.

In some embodiments, the peeled portion of the corneal epithelium does not include the Bowman's layer.

In some embodiments, the method further comprises collecting any of peeled tissue and released residue in the channel of the head.

In some embodiments, the released residue is a liquid.

In some embodiments, collecting comprises absorbing with an absorbent material at least partially coating the channel.

In some embodiments, the method further comprises orienting the elongated head with respect to the cornea to define the penetration depth of the elongated edge of the cutting blade into the corneal epithelium.

In some embodiments, orienting the elongated control and cutting blades substantially parallel to the tangent of the cornea causes the elongated cutting blade to penetrate to a relatively shallow depth and remove a thin layer of the cornea epithelium.

In some embodiments, orienting the elongated control and cutting blades substantially perpendicular to the tangent of the cornea causes the elongated cutting blade to penetrate to a depth corresponding to the height differential between the control and cutting blades and remove a layer of the cornea epithelium corresponding to the penetrated depth.

In some embodiments, peeling the cornea epithelium with the central section of the elongated edge of the cutting blade results in a thinner peeled slice, and peeling with the peripheral sections of the elongated edge of the cutting blade results in a thicker peeled slice.

In some embodiments, the method further comprises pressing the elongated edge of the control blade onto the cornea to flatten the surface of the cornea, and enclosing a portion of the flattened cornea within the gap, thereby peeling the epithelial tissue at a uniform thickness, wherein the gap is sufficiently small to prevent the cornea tissue enclosed therein from bouncing back to its naturally convex shape.

In some embodiments, the method further comprises maneuvering the elongated head over the corneal epithelium via a rigid handle coupled to the elongated head.

In some embodiments, the method further comprises performing any of: a refractive eye surgery, treating a myopia disorder, treating a hyperopia disorder, treating a astigmatism disorder, and treating a keratoconus disorder subsequent to the peeling step.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIGS. 2A-I show multiple views of device of FIGS. 1A-C, where FIGS. 2A-D and FIGS. 2F-I show cross-sections corresponding to those indicated in FIG. 2E, in accordance with an embodiment;

FIGS. 3A-C together illustrate the device of FIGS. 1A-C coupled to a handle, in accordance with an embodiment;

DETAILED DESCRIPTION

Disclosed herein is a device for removing a surface layer of the corneal epithelium ("epithelial tissue"), and a method for operating the device. A head formed from at least one cutting blade disposed substantially in parallel with a control blade is provided for controllably peeling or scraping the corneal epithelium. The cutting blade forms the distal extremity of the apparatus and is configured to peel the epithelial tissue, whereas the control blade limits the penetration of the cutting blade, thereby controlling the thickness of the peeled tissue to prevent damage to deeper, non-epithelial tissue layers. The two blades enclose a channel that collects any removed epithelial tissue or fluid. The head may be coupled to a handle, allowing a user or automated robot to maneuver the blades over the cornea.

Figures 1A, 1B:
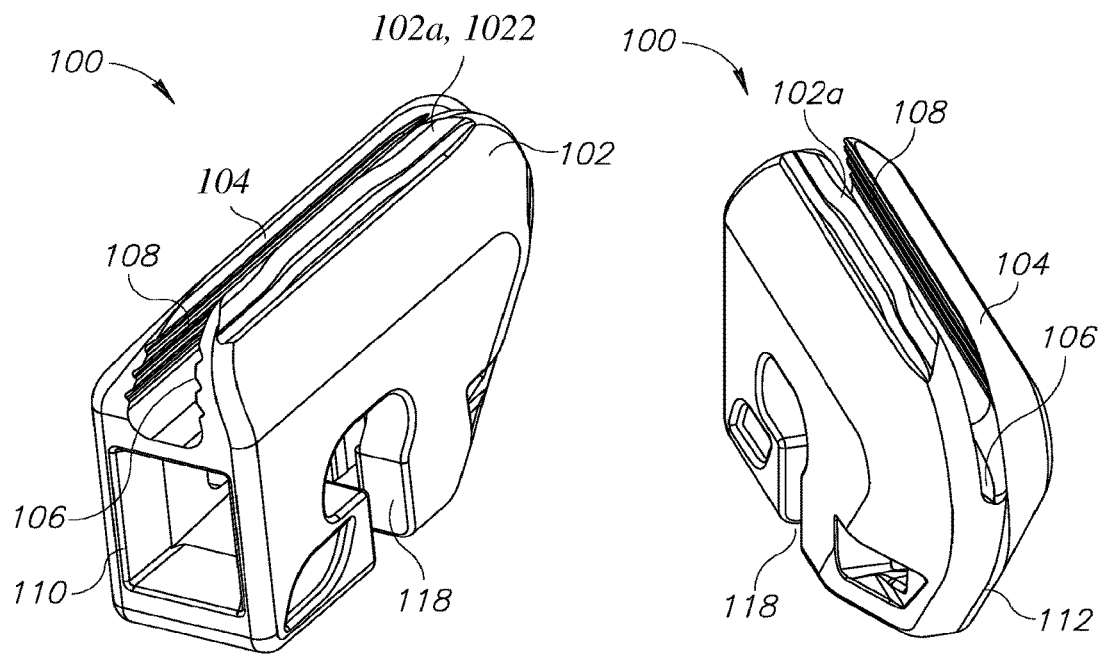
FIGS. 1A-C illustrate a device for removing a surface layer of the corneal epithelium, in accordance with an embodiment.
Figure 1C:
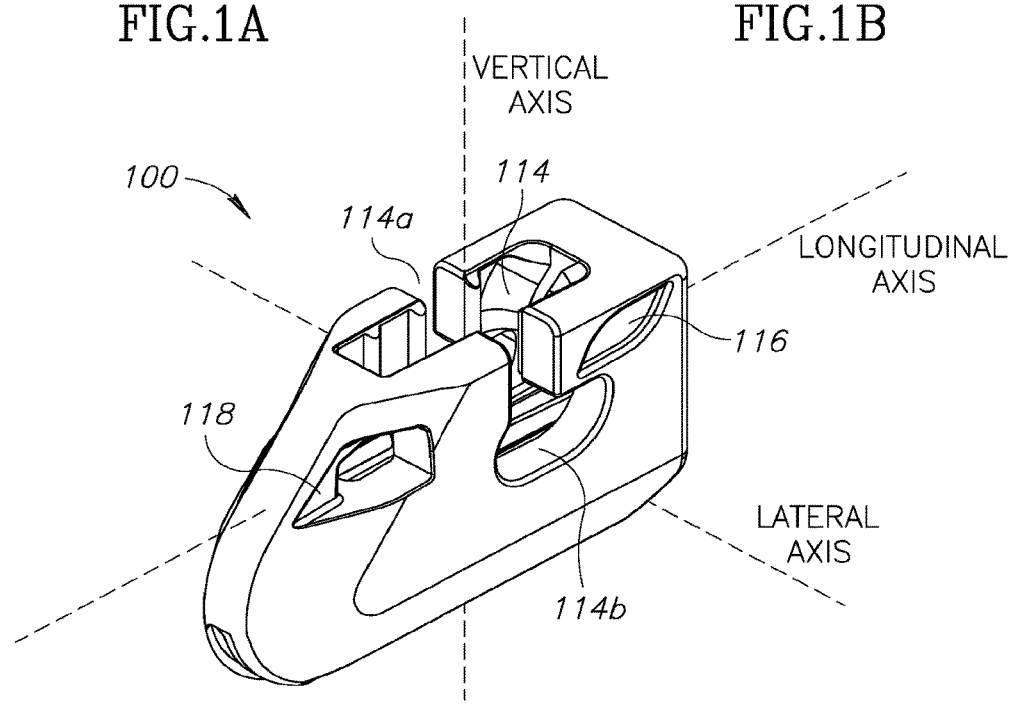

Reference is now made to FIGS. 1A-C which illustrate a device for removing a surface layer of the corneal epithelium, according to an embodiment. An elongated head 100 having substantially trapezoidal side faces is shown, with a longer distal end forming the top of the trapezoid substantially parallel to a shorter proximal end forming the bottom of the trapezoid. To facilitate the description of head 100, three orthogonal axes are indicated in FIG. 1C. The axis labelled 'vertical axis' runs from the proximal to the distal ends of head 100. The axis labelled 'longitudinal axis' runs from the anterior to the posterior ends of head 100. The axis labelled 'lateral axis' indicates the depth or thickness of head 100 and is perpendicular to both the vertical and the longitudinal axes.

The anterior side of head 100 tapers from the longer distal end to the shorter proximal end, forming a rounded acute angle at the anterior distal corner of the trapezoid and an obtuse angle at the anterior proximal corner of trapezoid. The acute angle may range from 25° to 75°. In one embodiment, the acute angle is 40°, or 45°, or 50°. The rounded angle at the anterior distal corner of the trapezoid may bulge outwards such that the anterior extremity is below the distal extremity of the trapezoid, forming a rounded protruding tip at the anterior face of head 100. In some embodiments, the rounded protruding tip protrudes along the longitudinal axis by 0.2 millimeters (mm), or 0.15-2.5 mm, or 0.1-0.3 mm from the anterior edge of the distal face of head 100. In some embodiments, the distance between the anterior extremity of the rounded protruding tip and the distal extremity of head 100 along the vertical axis is 0.2 mm, or 0.15-2.5 mm, or 0.1-0.3 mm. The posterior side of head 100 is substantially perpendicular to the distal end of head 100, forming a substantially orthogonal posterior wall to the parallel top and bottom of the trapezoid. The posterior distal corner of the trapezoid may be rounded along the plane defined by the longitudinal-vertical axes, resulting in a convex surface on the posterior face of head 100.

In some embodiments, the width or thickness of head 100 ranges between 2-5 millimeters (mm), or 2.5-4.5 mm, or 2.7-4 mm, or 2.8-3.5 mm, approximately 3 mm. In some embodiments, the height of head 100 from the proximal to the distal extremity ranges between 4-10 mm, or 5-8 mm, or 6-7 mm, or 6.2-6.7 mm.

The distal end of elongated head 100 is formed by an elongated control blade 102 positioned substantially in parallel along the longitudinal axis with at least one elongated cutting blade 104. In one embodiment, the angle between the control and cutting blades along the longitudinal axis may range between 10-45°, or optionally between 15-30°. Each of blades 102 and 104 comprises an elongated wedge spanning from the anterior to posterior sides head 100 and having a substantially triangular cross-sections, with a narrow, elongated distally disposed edge corresponding to the 'tip' of the triangle, and a wider, elongated proximally disposed base corresponding to the 'base' of the triangle. The outer wall of each of elongated control blade 102 and cutting blade 104 along the longitudinal axis is convex, forming a curved side of the triangle. The anterior distal corner of control and cutting blades 102 and 104 may taper, forming a rounded anterior distal corner of the trapezoidal face of head 100. Similarly the posterior distal corner of control and cutting blades 102 and 104 may taper, forming a rounded posterior distal corner of the trapezoidal face of head 100.

The elongated edge of cutting blade 104 extends distally beyond the elongated edge of control blade 102, and is a sharp edge that is configured to cut, peel, or scrape epithelial tissue, forming the distal extremity of head 100. In some embodiments, the external edges of cutting blade 104 form an acute angle of approximately 10°-50°, or 15°-45°, or 20°-40°, or 25°-35°, or approximately 30°. The elongated edge of cutting blade 104 may extend over the rounded anterior distal corner of head 100, providing a convex cutting surface that comprises the distal extremity and the anterior extremity of head 100.

The elongated edge of control blade 102 is disposed below the elongated edge of cutting blade 104 and is configured to press against the cornea without cutting the epithelial tissue, forming a barrier that limits the depth of penetration of the sharp edge of cutting blade 104. The external edges of control blade 102 may form a rounded corner having a radius ranging from 0.05 mm-0.1 mm, or one or more flat bands. The elongated edge of control blade 102 may extend over the rounded anterior distal corner of head 100, providing a continuous barrier to elongated edge of cutting blade 104. In one non-limiting embodiment, the elongated edge of control blade 102 is disposed 0.05-0.1 mm, or 0.1-0.15 mm, or 0.15-0.2 mm, or 0.2-0.25 mm, or 0.25-0.3 mm, or 0.3-0.5 mm, or 0.05-0.5 mm lower than the elongated edge of cutting blade 104. The elongated distal edges of blades 102 and 104 are separated by a substantially uniform gap (such as may vary between ±15% along its length) aligned with the lateral axis, running from the anterior to the posterior ends of head 100 and down the anterior distal rounded corner of head 100, forming the distal and anterior opening to an elongated channel 106 running from the anterior to the posterior ends of head 100. The width of the gap may range from 0.1-1.0 mm, or 0.8-0.2 mm, or 0.7-0.3 mm, or 0.6-0.3 mm, or 0.5-0.3 mm. In some embodiments, the width of the gap is 0.4 mm.

The distal edge 102a of control blade 102 may comprise a dull strip, or band 1022 extending along the distal surface of control blade 102. Possible widths for band 1022 may range from 0.05 to 0.25 mm. Band 1022 may be warped, having a non-uniform height differential with respect to the sharp edge of cutting blade 104, and resulting in a non-uniform height differential between elongated blades 104 and 102. In one non-limiting embodiment, distal edge 102a bulges higher in the middle section of the elongated edge of control blade 102, resulting in a smaller height differential at the middle sections of blades 102 and 104, and a larger height differential at the peripheral sections of blades 102 and 104. In some embodiments, the height differential between the distal edge of control blade 102a and the distal edge of cutting blade 104 at the bulge is 10%, or 20%, or 30%, or 40%, or 50% smaller than of the height differential at the peripheral sections of blades 102 and 104. Band 1022 may be parallel to the proximal base of head 100, or may slope gently, following the external convex surface of control blade 102. In some embodiments, the slope ranges from 10°-15°, or 15°-20°, or 20°-25°, or 25°-30°, or 30°-35°.

The penetration depth of cutting blade 104 may be defined by a combination of the orientation of the angle of head 100 with respect to the surface of the cornea, the width of the gap between blades 102 and 104 and their respective height differential. Thus, the penetration depth of cutting blade 104 may be controlled by adjusting the angle of control and cutting blades 102 and 104 with respect to the cornea, where orienting blades 102 and 104 substantially parallel to the tangent of the cornea causes cutting blade 104 to penetrate to a relatively shallow depth allowing the removal of a thin layer of epithelial tissue, and orienting blades 102 and 104 perpendicular to the tangent of the cornea, causes cutting blade 104 to penetrate to the height differential between blades 102 and 104, to remove a thicker layer of epithelial tissue corresponding to the penetrated depth. Similarly, the non-uniform height differential between control blade 102 and cutting blade 104 may be leveraged to peel a wider, or narrower layer off the cornea, where cutting with the central section of blade 104 having a smaller differential with control blade 102 results in a thinner peeled slice, and cutting with the peripheral sections of blade 104 having a larger differential with control blade 102 results in a thicker peeled slice.

In some embodiments, the length of the distal end of head 100, forming the top of the trapezoid, may range from 4-10 mm, or 5-9 mm, 6-8 mm, or approximately 7 mm. In some embodiments, the length of head 100 ranges between 5-13 mm, or 6-12 mm, or 7-11, or approximately 10 mm, having an outwardly protruding rounded anterior tip. In some embodiments, the height of the posterior side of head 100, along the longitudinal axis forming the orthogonal side of the trapezoid may range from 2-8 mm, or 4-6 mm. In some embodiments, control blade 102 prevents the penetration of cutting blade 104 from exceeding the thickness of the cornea epithelium, ranging between 50-70 microns (μm). In some embodiments, the axis of the height differential between control blade 102 and cutting blade 104 is substantially perpendicular to the axis of the gap between the blades, and the respective hypotenuse is at an angle of 20°, or 25°, or 30°, or 35°, or 40°, or 45°, or 50°, or 55°, or 60°, or 65°, or 65° with respect to the axis of the gap or the axis of the height differential.

Additionally, or alternatively, control blade 104 may be maneuvered to press onto the cornea to somewhat flatten its surface, allowing cutting blade 102 to peel the epithelial tissue at a uniform thickness. The gap between blades 104 and 102 may enclose a portion of the flattened cornea, and may be sufficiently small to prevent the pliable cornea tissue enclosed therein from bouncing back to its naturally convex shape.

The oppositely facing inner walls of the elongated wedge portions of blades 102 and 104 enclose channel 106 that is configured to collect any peeled epithelial tissue and/or other released or secreted residue. Channel 106 may have a sack-like cross-section, with a narrow elongated distal opening spanning from the anterior to posterior ends of head 100 and formed by the elongated distal edges of blades 102 and 104 corresponding to the gap therebetween, and a wider elongated proximal base formed by the concave inner walls of the wedge portions blades 102 and 104. The sack-like shape allows cut tissue and/or released fluid to withdraw proximally away from the cornea surface. Channel 106 may be provided with one or more parallel elongated grooves 108 embedded in the inner walls of channel 106 and extending substantially parallel to the edges of blades 102 and 104 across the length of head 100. Grooves 108 may be disposed at varying heights of the inner walls of channel 106, and may increase the surface area of the walls of channel 106, to enhance the capillary action of channel 106. In one embodiment, channel 106 is provided with one, two, three, or more grooves 108.

In some embodiment, the base of channel 106 is 300%, or 400%, or 500%, or 600%, or 700%, or 800%, or 900%, or 1000% wider than the gap forming the distal opening to channel 106. In some embodiments, the depth or height of channel 106 from the distal opening to the base ranges from 0.1-0.8 mm, or 0.2-0.7 mm, or 0.3-0.6 mm, or 0.4-0.5 mm.

Channel 106 may be at least partially coated with an absorbent substance, such as a sponge-like material suitable for absorbing fluid, such as tear solution, water, medication fluid that may be released from the cornea during a cutting procedure and/or any peeled tissue. The absorbent substance may increase the rate of fluid evacuation from the cornea surface during a cutting procedure, allowing for a relatively dry cornea surface that may reduce the chance of uncontrolled sliding of cutting blade 104 of the cornea during the cutting procedure. In one embodiment, the absorbent substance is disposed within grooves 108 as elongated absorbent channels. Additionally or alternatively, the elongated base of channel 106 may be fully or partially coated with the absorbent material, providing an absorbent pocket for any cut tissue and/or released fluid.

FIG. 1A shows a substantially flat posterior end of head 100. The posterior opening of channel 106 has the sack-like shape as described above, with a narrow distal opening defined by the distal edges of blades 102 and 104, and a wider base defined by the inner convex walls of the proximal wedges of blades 102 and 104. The posterior end of head 100 may be disposed with a window 110 positioned proximally with respect to channel 106. Window 110 may be square or rectangular in shape, having straight sides and rounded corners.

Referring to FIG. 1B, a tapered anterior end 112 of head 100 is shown, formed by the externally convex anterior walls and rounded anterior distal corners of blades 102 and 104. A portion of the anterior distal rounded corner of blade 104 may be hollowed out, forming a narrow groove comprising an anterior side opening of channel 106. The narrow anterior opening of channel 106 may prevent any peeled epithelial tissue collected therein from falling out from the anterior end of head 100, allowing the user to maneuver head 100 while performing the cutting procedure, accordingly. Similarly, the rounded and tapered anterior distal corner of head 100 may allow the user to maneuver head 100 over the cornea during the cutting procedure, to accurately position control and cutting blades 102 and 104 on the surface of the cornea.

Reference is now made to FIG. 1C which shows the bottom proximal face of head 100 having a recess 114 that is configured to engage with a handle, and which will be described in greater detail below. Recess 114 may have any suitable shape for engaging with the handle. In one embodiment, recess 114 forms a cross-shape on the proximal face of head 100, with a longer rectangular portion of the cross disposed longitudinally along the length and enclosed by the proximal face of head 100, and a shorter rectangular portion of the cross disposed horizontally and dividing the proximal face of head 100 into two sections forming two gaps 114a. Gaps 114a may extend to the sides of head 100 to form two hollowed out lips 114b on each trapezoidal face of head 100. Gaps 114a with lips 114b may penetrate head 100 along the lateral axis, forming hollowed out windows. Head 100 may be provided with additional recesses, such as recesses 116 disposed on either side of head 100 at the proximal posterior corner of head 100 and recesses 118 disposed on either side of head 100 at the proximal anterior corner of head 100. Recesses 116 may have a parallelogram shape and may be positioned on a flat surface of head 100, whereas recesses 118 may be trapezoidal in shape and may be positioned on the contoured, tapered anterior surface of head 100 wrapping around the external surface of head 100 towards its tapered anterior edge. Recess 116 and/or 118 may penetrate though head 100 along the lateral axis, forming one or more hollowed out windows.

Blades 102 and 104 may be composed of a biocompatible polymer, or metal and may be coated with a hydrophilic material to enhance the collection of any released fluid within chamber 106. Metal blades may be manufactured with a high surface finish, to reduce inflammation and/or an engraving effect on the cornea.

Head 100 may be configured to be used for a limited number of procedures, such as one, two or more procedures, and disposed thereafter. Alternatively, head 100 may be suitable for sterilization and may be used any number of times.

In one embodiment head 100 has three distally disposed blades: two control blades 102 positioned on either side of a central cutting blade 104. The blades may be substantially similar to those described above, with the notable difference that cutting blade 104 is a double-sided blade, allowing for controlled, bidirectional peeling of the epithelium. Control blades 102 may be symmetrically disposed about central cutting blade 104, having the same features described above, symmetrically positioned about central cutting blade 104. Alternatively, control blades 102 may have different gaps and differential heights with respect to central cutting blade 104, allowing for greater variability to control the thickness of the peeled tissue.

Optionally, the contact surface area of the triple-bladed head is smaller than the contacting surface area the double bladed head. The number of blades and their respective disposition with respect to each other may be selected to obtain a desired contact surface area with the cornea.

Reference is now made to FIGS. 2A-I which show multiple cross-sectional views of head 100, corresponding to the slices indicated in FIG. 2E. FIGS. 2A-D show the narrow anterior opening of channel 106, and FIGS. 2F-I show the wider sack-shaped posterior opening of channel 106. The differential height as well as the gap between control blade 102 cutting blade 104 is clearly shown. FIGS. 2F-I show grooves 108 disposed at varying heights along the inner walls of channel 106.

FIGS. 2B-D show multiple cross-sectional views of recess 114. In particular, FIG. 2D is shown engaged with a handle coupled to head 100.

Reference is now made to FIGS. 3A-C which together illustrate head 100 coupled to a handle 200 that allows the user to maneuvering head 100 over the cornea, according to an embodiment. FIG. 3A shows handle 200 disengaged from head 100, FIG. 3B shows handle 200 engaged with head 100, and FIG. 3C shows a close-up 204 of handle 200 engaged to head 100. Handle 200 may taper towards its distal end, and may be disposed with a clip-like end comprising two flat, disk-like tips 202 that are wider than the tapered portion of handle 200. Tips 202 may be used to couple handle 200 to head 100 by inserting tips 202 with their flat sides oriented longitudinally with head 100 into the longer rectangular portion of the cross-shape of recess 114. Handle may be rotated by 90° to align tips 202 with their flat sides oriented with the shorter rectangular portion of the cross-shape of recess 114. Tips 202 may be separated and may couple with head 100 by locking into either end of the longer rectangular portion. Alternatively, the head 100 and handle 200 are integrally formed. Optionally, recesses 116 and 118 may be used to engage and/or release handle 200 from head 100.

Alternatively, head 100 may engage with handle 200 using any other suitable means, such as via a threaded connection, a mounting, a joint, and/or any other type of coupling. The coupling between head 100 and handle 200 may fixate the orientation of head 100 with respect to handle 200, such that the movement of head 100 is actuated solely by the user's maneuvering of handle 200. Handle 200 may be rigid to allow transferring the user's motion onto head 100. Alternatively, head 100 may be at least partially rotatable about handle 200.

Optionally, handle 200 may be reusable, or disposable and may be suited for sterilization.

Figure 4C:
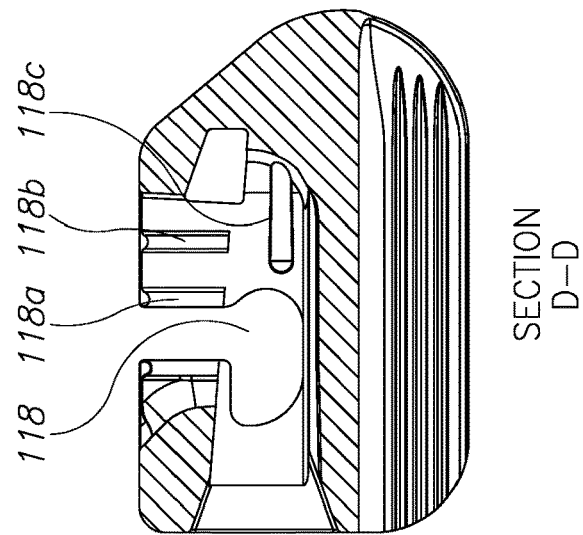
FIGS. 4A-C show three additional cross-sectional views of the device of FIGS. 1A-C, in accordance with an embodiment.
Figure 4B:
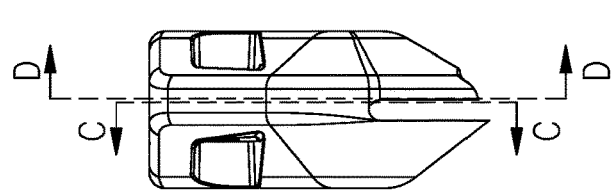
Figure 4A:
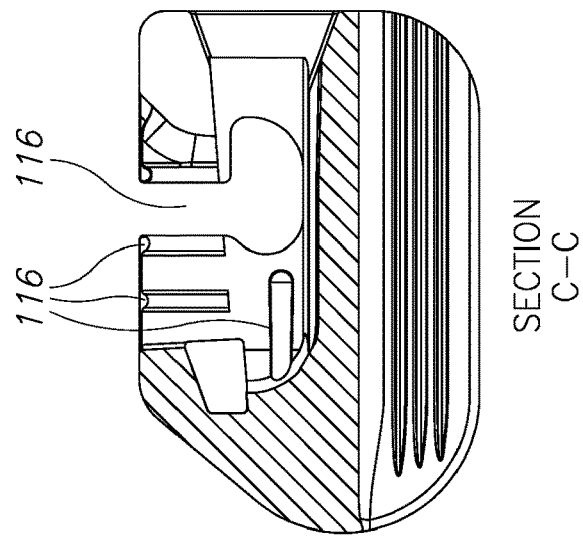

Reference is now made to FIGS. 4A-C which show three cross-sectional views of head 100 with detailed views of recesses 114, 116, and 118 that are configured to engage and/or release handle 200 from head 100. Recess 118 may include one or more rachet-type features that may alternately lock and release handle 200 with head 100.

Figure 5:
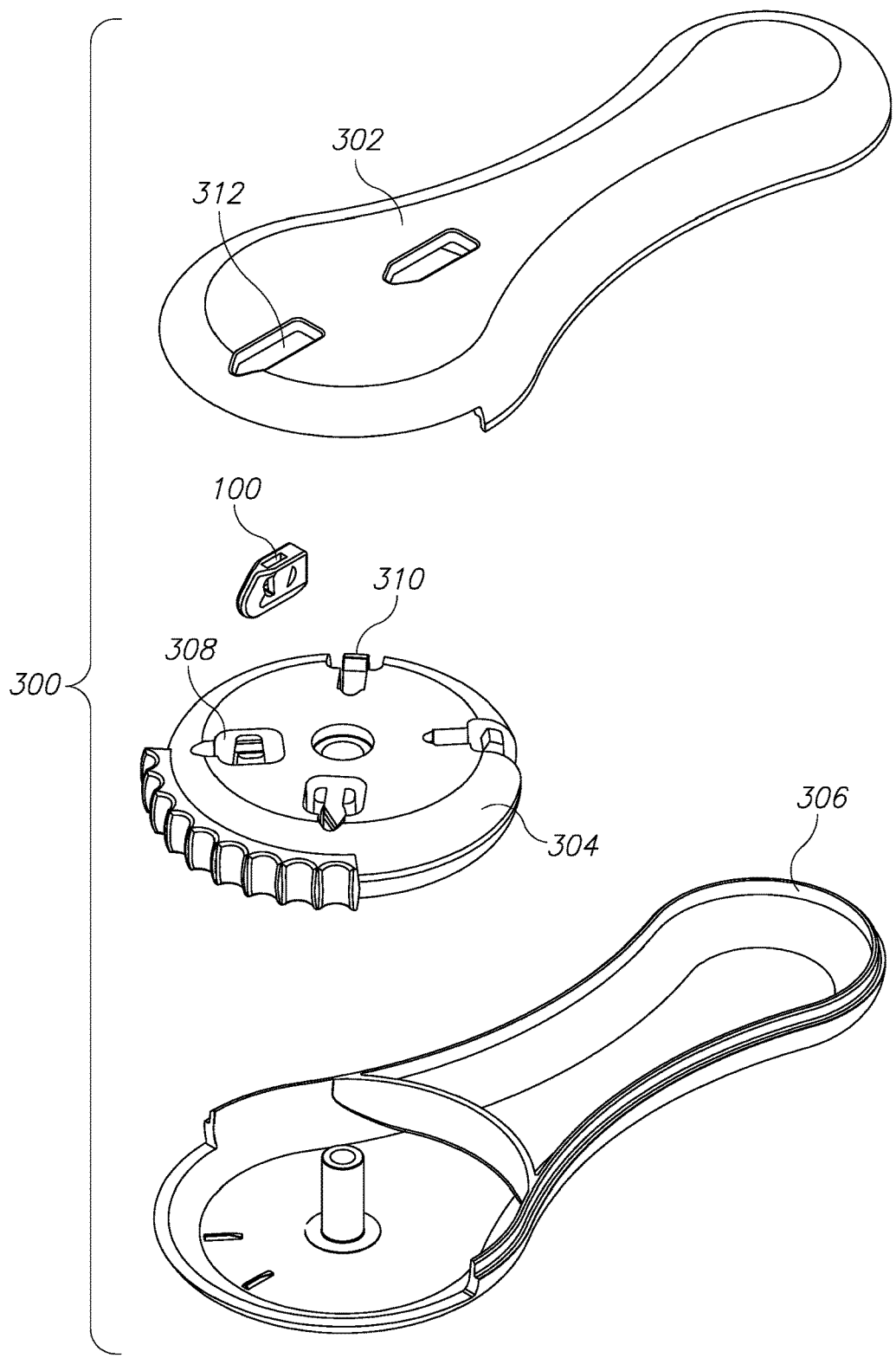
FIG. 5 shows an exploded view of a holding cassette configured to store one or more of the devices of FIGS. 1A-C, in accordance with an embodiment.

Reference is now made to FIG. 5 which shows an exploded view of holding cassette 300 configured to store one or more of heads 100, according to an embodiment. Cassette 300 comprises a top cover 302, a rotatable cartridge 304, and a bottom cover 306. Top 302 and bottom 306 may enclose cartridge 304, leaving a gap that exposes cartridge 304 allowing the user to rotate cartridge 304 and couple handle 200 to head 100. Cartridge 304 may include multiple compartments 308 enclosed therein that are each configured to store one of heads 100 oriented with recess 118 facing outwards. Cartridge 304 may be rotatable via a serrated edge 310 allowing for easy gripping by the user. Rotating cartridge 304 may align one of compartments 308 with one of openings 310 to expose head 100 in the gap, and allow head 100 to be coupled to handle 200 while leaving the edges of blades 102 and 104 untouched.

Cassette 300 may protect heads 100 stored therein, and may be provided with one or more clips or prongs that are configured to secure head 100 within cassette, such as by engaging with any of proximally disposed window 110, and/or recesses 116 and 118 without having contact with the distal edges of any of blades 102 and 104. Alternatively, the clips may secure head 100 using pressure, or any other suitable technique.

Multiple heads 100 housed within a cassette 300 and one or more handles 200 may be provided to the user as a kit, allowing the user to engage head 100 to handle 200 according to need.

Cassette 300 may store multiple heads each having a different size, gap, blade-height differential corresponding to varying cornea sizes, shapes, and/or conditions, allowing the user to apply the correctly sized head 100 according to need. The kit may include multiple cartridges storing multiple heads 100 of different sizes. Similarly, the kit may include multiple different handles 200 having different lengths.

The following is a method for modifying the corneal epithelium, according to an embodiment.

Optionally, the method may be performed prior to a refractive eye surgery, for treating disorders such as myopia, hyperopia, astigmatism, keratoconus or other. The refractive surgery may include, for example, procedures for reshaping the curvature of the cornea, for example using surface ablation methods such as Photorefractive Keratectomy (PRK), Photo Therapeutic Keratectomy (PTK), Laser Assisted Sub Epithelium Keratomileusis (LASEK), EPI-LASEK, Advanced Surface Ablation (ASA) techniques.

Optionally, the method may comprise positioning a plurality of blades such as two, three, or a higher number of blades on a surface of the cornea. Optionally, the blades are configured on a head of a device as described above. Optionally, the head is coupled to a handle which is manually maneuvered by a user.

Optionally, the method comprises modifying the epithelium. Optionally, modifying includes peeling/removing the epithelium. Optionally, modifying includes reducing a thickness of the epithelium. Optionally, a thickness of the removed layer varies between different portions of the cornea surface, for example a thicker layer is removed from a center of the cornea and a thinner layer is removed from the periphery. Alternatively, a thickness of the removed layer is constant and substantially even for the various treated portions of the cornea surfaces. Optionally, modifying includes reshaping the epithelium. Optionally, modifying does not affect the Bowman's layer under the epithelium. Alternatively, modifying includes removing at least a portion of the Bowman's layer. In some embodiments, modifying does not cause damage to the stroma.

Optionally, modification is obtained by collecting epithelial tissue. In some embodiments, modification is obtained by peeling the epithelial tissue. Optionally, peeling of epithelial tissue is carried out by moving the blades across a surface of the cornea. Optionally, moving comprises stroking type movement, saccadic movement, one-directional movement, two directional movement. In some embodiments, the blades are caused to slide across the cornea surface.

In some embodiments, the blades are configured to form a slope in the epithelial tissue during their movement, for example a slope between the center of the cornea and a circular periphery of the cornea. Optionally, the slope angle ranges between 10-30 degrees, such as 12 degrees, 18 degrees, 25 degrees, or intermediate, larger or smaller angles. A potential advantage of producing a slope by movement of the blades across the cornea surface may include inducing cell growth, which may provide a faster healing rate of the tissue, for example following a refraction procedure. An effect of the slope may include faster regrowth of cells at the bottom of the slope, for example at the cornea center, which may accelerate healing.

Optionally, removed epithelial tissue and/or fluid are collected, for example drained into a channel between the blades.

Optionally, the surface of the cornea is dried. In some embodiments, drying is performed by collecting fluid during movement of the device across the cornea, for example by using one or more absorbing elements, for example as further described herein. Optionally, drying is obtained by draining fluid utilizing capillary action of a channel defined in between the blades.

Optionally, after removal and/or other modification of the epithelial tissue, and/or once the cornea is dry (for example relative to a natural state of the cornea), a refractive surgery is performed.

Figure 6:
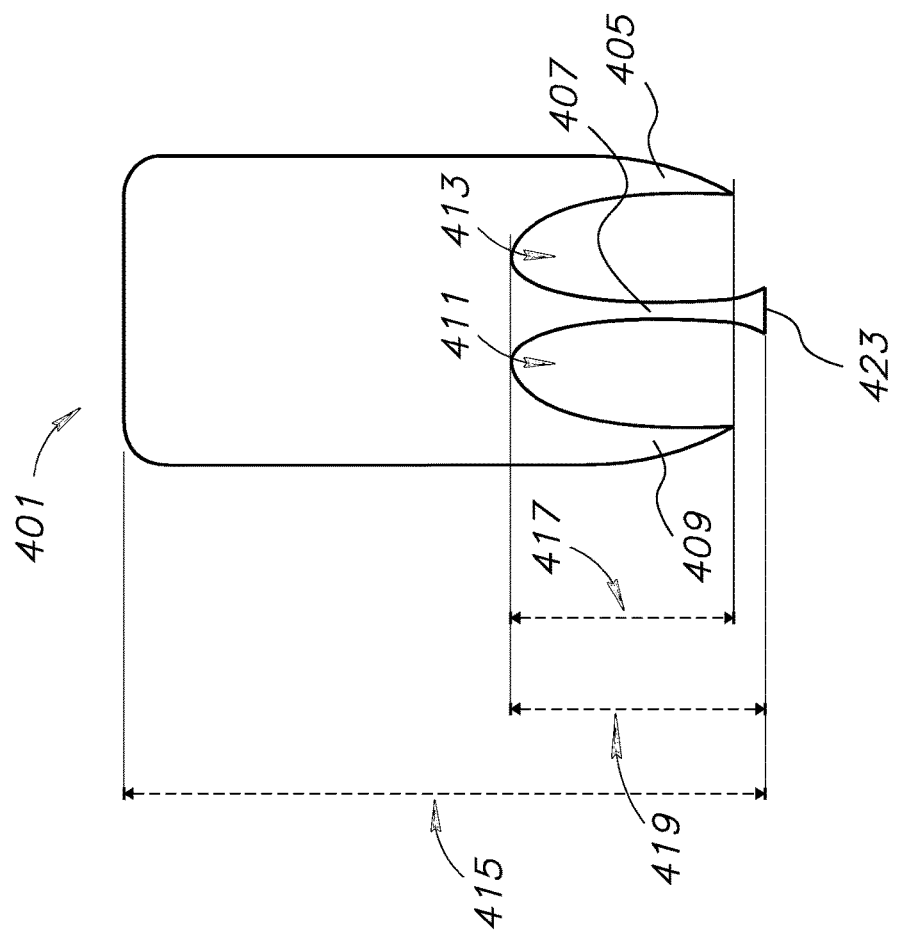
FIG. 6 shows a triple-bladed device for removing a surface layer of the corneal epithelium, in accordance with an embodiment.

FIG. 6 is a front view of an exemplary head of a device for modifying the corneal epithelium, comprising or consisting of three blades, according to some embodiments of the invention.

In some embodiments, head 401 comprises a plurality of blades, such as blades 405, 407, 409 shown herein, disposed at a distal end of head 401. In some embodiments, blade 407 comprises a distal contacting surface or edge such as contacting surface 423. In some embodiments, two channels are defined between the walls of the base portions of adjacent blades, a first channel 411 defined between the base portions of blades 409 and 407, and a second channel 413 defined between the base portion of blades 405 and 407.

In some embodiments, channels 411 and 413 extend in a proximal direction, for example extending over ⅛ to ½ of a height 415 of head 401, the height measured between the proximal and distal ends of the head.

In some embodiments, blades 405, 407, 409 are formed with different heights with respect to each other (the height being measured, for example, from a proximal end of the channels formed between the blades, to a contacting surface of each blade which engages the cornea). Optionally, a height difference between the blades determines a depth of penetration of the blades with respect to a surface of the cornea. In some embodiments, the blades are configured so that a first and/or second blade limit a depth of penetration of a third blade with respect to a surface of the cornea. For example, as shown in this figure, the two outermost blades 405 and 409 each act as a positioning (also "control") blade for middle blade 407, which is double-edged. In some embodiments, a positioning blade is formed with a height 417 that is shorter than height 419 of middle blade 407, for example 10%, 20%, 30%, 40%, or intermediate, larger or smaller percentages shorter. Optionally, height 419 of middle blade 407 ranges between, for example, 2-3 mm, such as 2 mm, 2.2 mm. 2.7 mm, or intermediate, longer or shorter heights, and height 417 of positioning blade 405 is shorter than height 419 by, for example, 0.15-0.2 mm. In some embodiments, the height differences between the blades maintain a fixed positioning of the blades with respect to the curved surface of the cornea. A potential advantage of one or more blades configured for limiting a depth of penetration of another blade may include preventing a blade from damaging deeper layers of tissue, for example layers underneath the epithelium. The fixed positioning may provide additional safety, for example by reducing damage to deeper tissue layers which in turn may be caused by a user applying excessive pressure when maneuvering the device over the cornea. A potential advantage of the blade arrangement may include reducing an effect of force applied by a user on the depth of the blades within the fluidic layer of the epithelium. Positioning blade 405 and/or positioning blade 409, act to stabilize blade 407 on the corneal surface. Optionally, blade 405 acts to stabilize blade 407 when peeling is performed in a first direction, and blade 407 acts to stabilize blade 407 when peeling is performed in an opposite direction. Potentially, even uncontrolled movement of the device across the cornea will not cause substantial damage to deeper tissue layers, and may reduce the risk of tearing cornea tissue during peeling.

In some embodiments, a positioning blade such as blade 405 defines an entrance angle α of middle blade 407 with respect to the cornea. Entrance angle α is defined, for example, with respect to a horizontal axis, passing through a point or line formed by one of the edges of contacting surface 423 of blade 407 (the edges are the right and left corners of contacting surface 423 shown in the figure). Optionally, the opening of angle α is set by the positioning of the contact surface of blade 305 with respect to the horizontal axis. Optionally, angle α ranges between, for example, 38-55 degrees, such as 40 degrees, 47 degrees, 52 degrees or intermediate, larger or smaller angles.

In some embodiments, blades 405 and 409 are identical, forming a symmetrical head. Alternatively, blade 405 is different from blade 409 in height and/or in a size of the contacting surface or edge and/or in a distance of the contacting surface of the blade from the contacting surface of middle blade 407. Optionally, a non-symmetrical configuration of the head provides for treating in one direction in a different manner than the other direction, for example peeling a thicker layer of tissue when moving the head in a first direction, and a thinner layer when moving the head in a second direction. Optionally, the arrangement of the blades and their respective heights, contacting surfaces, distances between the blades and/or other parameters are selected according to a topography of the cornea surface.

In some embodiments, the device is moved across the cornea to peel the epithelial tissue. Optionally, movement is performed on a plane tangential to a curvature of the cornea, for example in one or two directions (left and/or right directions) that are substantially transverse to height 415 of head 401. For the exemplary head shown in this figure, movement to the right will cause the right edge of contacting surface 423 of blade 407 to peel epithelial tissue which will collect within channel 413, while movement to the left will cause the left edge to peel epithelial tissue which will collect within channel 411. Movement to the right is defined by the positioning of blade 405 with respect to blade 407 and with respect to the cornea, while movement to the left is defined by the positioning of blade 409 with respect to blade 407 and with respect to the cornea. Optionally, the peeled tissue is collected on the side walls of blade 407 as the device is advanced across the corneal surface, optionally accumulating within the draining channels 411 and 413.

In some embodiments, the walls of the blades which define channels 411 and 313 comprise one or more slits (not shown in this figure). The slits act to increase the total surface area of the walls that define the channel, and may increase the capillary forces of the channel, causing fluid and/or removed tissue to adhere to the channel and to be sucked in the proximal direction and away from the cornea surface. In some embodiments, a channel is conical, comprising an opening which widens in a proximal direction. A potential advantage of the conical configuration may include causing fluid and/or tissue to adhere to the channel walls and be drawn up into the channel at the contact area between the cornea and the channel, in which the opening is of a relatively small diameter. The capillary action may decrease as the channel widens in a proximal direction.

In some embodiments, blades 405, 407, and/or 409 are composed of a biocompatible polymer. Alternatively, in some embodiments, the blades are composed of metal. Optionally, the metal blades are manufactured with a high surface finish, to reduce inflammation and/or an engraving effect on the cornea. In some embodiments, the material of which the blades are composed of or are coated with is hydrophilic, for increasing the effect of collecting fluid.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements. Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A device comprising:
   an elongated head having a length ranging between 5-13 millimeters, and having a distal end having a length ranging from 4-10 millimeters formed by an elongated edge of a cutting blade positioned substantially in parallel with an elongated edge of a control blade,
   wherein the elongated edges of the respective control and cutting blades are separated by a substantially uniform gap having a width ranging between 0.02 to 0.2 mm and forming a distal opening to an elongated channel running from an anterior end to a posterior end of the head, and
   wherein the elongated edge of the cutting blade extends distally beyond the elongated edge of the control blade providing a height differential ranging from 0.05-0.5 mm between the elongated edge of the cutting blade and the elongated edge of the control blade, and
   wherein the elongated edge of the cutting blade is sharp, having outer edges forming an acute angle ranging between 10°-50°, and configured to cut a bodily tissue, and
   wherein the elongated edge of the control blade is dull, having outer edges forming a rounded corner with a radius ranging from 0.05 mm-0.1 mm, and configured to form a barrier that limits the depth of penetration of the elongated edge of the cutting blade into the bodily tissue, and wherein the elongated channel is enclosed by two oppositely facing inner walls of the control blade and the cutting blade, and wherein the inner walls are concave, and wherein the elongated channel formed by the concave inner walls has a sack-like cross section having a broad proximal base and a narrow distal opening, wherein the channel is configured to collect any combination of peeled epithelial tissue and released residue, and wherein the channel is disposed with one or more elongated grooves embedded in the inner walls of the channel and extending substantially parallel to the elongated edges of control and cutting blades and increasing the surface area of the inner walls of channel.

2. The device of claim 1, wherein the elongated edge of the control blade comprises a band having a non-uniform height differential with respect to the elongated edge of the cutting blade.

3. The device of claim 2, wherein a combination of the width of the gap and the height differential between the elongated edge of the cutting blade and the elongated edge of the control blade defines the depth of penetration of the edge of the cutting blade.

4. The device of claim 3, wherein the orientation of an angle of the head with respect to a surface of the bodily tissue further defines the depth of penetration of the edge of the cutting blade.

5. The device of claim 2, wherein the height differential is smaller at a middle section of the elongated edges of the control and cutting blades, and larger at a peripheral section of the elongated edges of the control and cutting blades.

6. The device of claim 1, wherein the elongated edge of the control blade is configured to press onto a cornea to flatten its surface, and wherein the gap is configured to enclose the flattened cornea and prevent the flattened cornea enclosed therein from bouncing back to a naturally convex shape.

7. The device of claim 1, wherein the channel is at least partially coated with an absorbent substance that is suitable for absorbing fluid.

8. The device of claim 1, wherein the grooves are disposed at varying heights of the channel.

9. The device of claim 8, wherein the one or more grooves are disposed with an absorbent substance that is suitable for absorbing fluid.

10. The device of claim 1, further comprising a handle, wherein the head is disposed with a proximal recess that is configured to engage with the handle.

11. The device of claim 10, wherein the proximal recess is configured to release the engaged handle.

12. The device of claim 10, wherein the handle is rigid and transfers a motion applied to the handle to the head.

13. The device of claim 1, wherein the head is disposed with one or more recesses that are configured to engage with one or more prongs that are configured to secure the head, and wherein the recesses are disposed at a proximal end of the head and engaging with the prongs comprises having no contact with the distal edges of the blades.

14. The device of claim 1, wherein the anterior end of the head is tapered and is formed by the externally convex anterior walls and rounded anterior distal corners of the control blade and the cutting blade.

15. The device of claim 14, wherein a portion of the anterior distal rounded corner of the control blade is hollowed out, forming a narrow groove comprising an anterior side opening of the channel.

16. The device of claim 1, wherein the bodily tissue is the cornea.

17. The device of claim 1, further comprising a second control blade, wherein the cutting blade is a double-sided blade, and wherein the two control blades are disposed on either side of the double-sided cutting blade.

18. A device comprising:
an elongated head having a length ranging between 4-10 millimeters, and having a distal end having a length ranging from 5-13 millimeters formed by an elongated edge of a cutting blade positioned substantially in parallel with an elongated edge of a control blade, wherein the elongated edges of the respective control and cutting blades are separated by a substantially uniform gap having a width ranging between 0.02 to 0.2 mm and forming a distal opening to an elongated channel running from an anterior end to a posterior end of the head, and wherein the elongated edge of the cutting blade extends distally beyond the elongated edge of the control blade providing a height differential ranging from 0.05-0.5 mm between the elongated edge of the cutting blade and the elongated edge of the control blade, and wherein the elongated edge of the cutting blade is sharp, having outer edges forming an acute angle ranging between 10°-50°, and configured to cut a bodily tissue, and wherein the elongated edge of the control blade is dull, having outer edges forming a rounded corner with a radius ranging from 0.05 mm-0.1 mm, and configured to form a barrier that limits the depth of penetration of the elongated edge of the cutting blade into the bodily tissue, and wherein the elongated edge of the control blade comprises a band having a non-uniform height differential with respect to the elongated edge of the cutting blade; and wherein the non-uniform height differential is smaller at a middle section of the elongated edges of the control and cutting blades, and larger at a peripheral section of the elongated edges of the control and cutting blades.

* * * * *